United States Patent [19]

Chen et al.

[11] Patent Number: 5,481,011

[45] Date of Patent: Jan. 2, 1996

[54] PROCESS FOR PREPARING N-PROTECTED AMINO ACID α-HALOMETHYL KETONES AND ALCOHOLS FROM N-PROTECTED AMINO ACID ESTERS

[75] Inventors: Ping Chen; Peter T. W. Cheng, both of Lawrenceville, N.J.; Steven H. Spergel, Bensalem; Joel C. Barrish, Holland, both of Pa.; John K. Thottathil, Robbinsville, N.J.; Robert Zahler, Pennington, N.J.; Richard P. Polniaszek, South Brunswick, N.J.; Xuebao Wang, East Brunswick, N.J.

[73] Assignee: Bristol-Myers Squibb Company, New York, N.Y.

[21] Appl. No.: 355,373

[22] Filed: Dec. 13, 1994

[51] Int. Cl.$^6$ ............... C07D 301/02; C07D 303/12; C07D 303/36

[52] U.S. Cl. ............................ 549/514; 560/160

[58] Field of Search ............................ 549/514

[56] References Cited

FOREIGN PATENT DOCUMENTS

| | | |
|---|---|---|
| 346847 | 12/1989 | European Pat. Off. |
| 580402 | 1/1994 | European Pat. Off. |
| 2815182 | 10/1978 | Germany ............... 549/514 |
| 3932352 | 4/1990 | Germany ............... 549/514 |
| 1290787 | 9/1972 | United Kingdom. |
| 1335317 | 10/1973 | United Kingdom. |
| WO93/23388 | 11/1993 | WIPO. |

OTHER PUBLICATIONS

Barluenga et al, "J. Chem. Soc.", Perkin Trans. 1, 1991 pp. 297–309.
Demuth, *J. Enzyme Inhibition*, 3:249–278 (1990) (review).
Evans, et al, *J. Org. Chem.*, 50:4615–4625 (1985).
Luly, et al, *J. Org. Chem.*, 52:1487–1492 (1987).
Kowalski, et al, *J. Org. Chem.*, 50:5140–5142 (1985).
Barluenga, et al, *J. Chem. Soc., Chem. Commun.*, pp. 969–970 (1994).
Kowalski, et al, *J. Org. Chem.*, 57:7194–7208 (1992).
Reutrakul, et al, *Chemistry Letters*, pp. 209–212 (1979).
Wheeler, et al, *J. Med. Chem.*, 22:657–661 (1979).
Kakeya, et al, *Chem. Pharm. Bull.*, 32:692–698 (1984).
Harada, et al, *Syn. Commun.*, 24:767–772 (1994).

*Primary Examiner*—Joseph E. Evans
*Attorney, Agent, or Firm*—Samuel J. DuBoff

[57] ABSTRACT

The present invention relates to a novel method useful for the conversion of amino acids to halomethylketones, which are then converted to amino acid epoxides. Such epoxides are important intermediates for the synthesis of inhibitors of renin and HIV protease, which are particularly useful in the treatment and/or prevention of HIV infection (AIDS).

16 Claims, No Drawings

PROCESS FOR PREPARING N-PROTECTED AMINO ACID α-HALOMETHYL KETONES AND ALCOHOLS FROM N-PROTECTED AMINO ACID ESTERS

BACKGROUND OF THE INVENTION

In addition to their use as irreversible active site inhibitors of certain cysteine and serine-containing proteases (review: Demuth, *J. Enzyme Inhibition,* 1990, 3, 249), amino acid α-halomethyl ketones can be converted into N-protected amino acid epoxides, important intermediates for the synthesis of inhibitors of enzymes such as renin (Evans, et al., *J. Org. Chem.* 1985, 50, 4615; Luly, et al. *J. Org. Chem.* 1987, 52, 1487) and HIV protease (Handa, et al., EP 346847; Gordon, et al., published European patent application EP 580402). Standard methodology to prepare N-protected amino acid α-halomethyl ketones and alcohols (e.g. see Gordon, et al, EP 580402) involves initial treatment of N-protected amino acids I (Reaction Scheme 1) with an alkyl chloroformate, such as isobutyl chloroformate, and a tertiary amine, such as N-methyl morpholine, followed by addition of a diazomethane/diethyl ether solution to give an N-protected amino acid α-diazoketone II.

Reaction Scheme 1

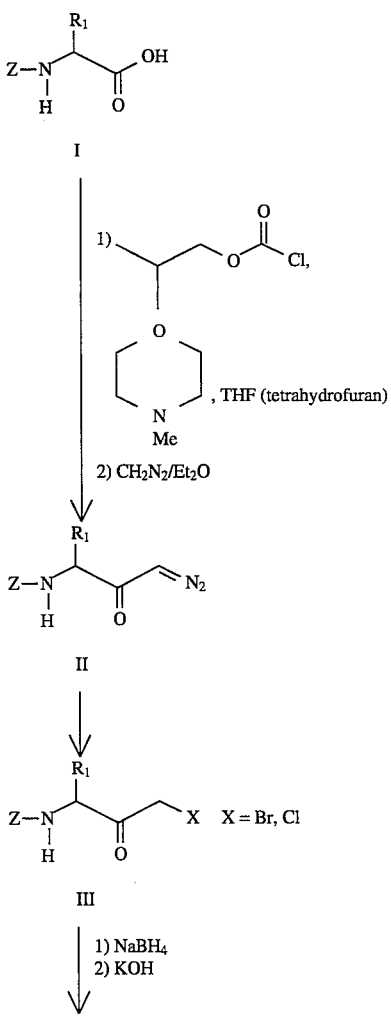

-continued
Reaction Scheme 1

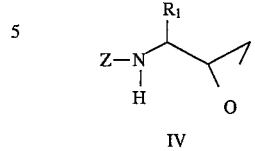

Treatment of II with a mineral acid such as HCl or HBr then gives the desired α-haloketone III. Intermediate III can be converted to epoxide IV by reduction with a hydride reducing agent such as $NaBH_4$ and treatment of the resulting halohydrin with base, such as potassium hydroxide. As diazomethane is a hazardous reagent, methods to prepare compounds III which avoid the use of diazomethane would be advantageous. Kowalski et al. (*J. Org. Chem.* 1985, 50, 5140) have prepared α-bromoketones VII (Reaction Scheme 2) from ester (V) where $R_2$=aryl, heteroaryl, lower alkenyl, lower alkynyl, and lower alkyl (not including amino substituted alkyl) by treatment of the ester with 2 equivalents of the anion derived from dibromomethane, followed by addition of 1.5 equivalents of n-BuLi to the intermediate VI and hydrolysis.

When this method was used to convert aminoester (XI) to a halomethylketone (XIII) (see page 7 herein), the resulting yields were only modest.

It has since been surprisingly and unexpectedly found that replacement of the n-BuLi by an excess of the dihalomethane anion instead, specifically chloroiodomethane, results in greatly enhanced yields of 80% or more.

Reaction Scheme 2

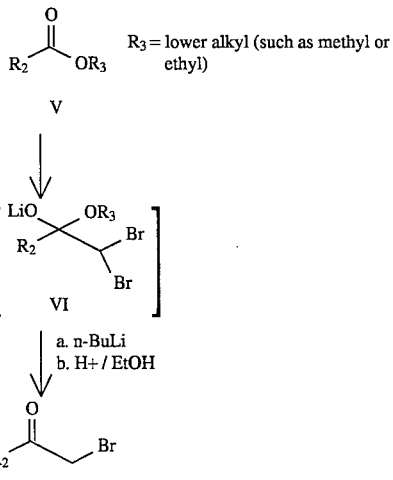

Barluenga, et al. (JCS *Chem. Commun.* 1994, 969) have prepared the α-chloroketone X (Reaction Scheme 3) from the α-amino ester VIII by treatment with 2 equivalents of the anion IX, generated from metallation of chloroiodomethane with methyl lithium in diethyl ether, followed by hydrolysis. Note that the anion IX is different than the anion XII (Reaction Scheme 4), generated from deprotonation of chloroiodomethane with a dialkylamide base such as LDA (i.e. lithium diisopropylamide amide), described in the present invention. Moreover, the Barluenga process has only been demonstrated for N,N-dibenzyl protected aminoester (Compound VIII). It is not clear that the process would work for N-carbamate protected aminoesters (Compound XI) as used herein. The Compounds XI are more easily prepared and deprotected if needed and allow for the presence of an active hydrogen in the nitrogen atom. Also, deprotonation of $X_1 CH_2X_2$ to form the anion $X_1 CH(Li) X_2$, which is our Compound XII, may be easier to carry out efficiently on a larger scale compared to transmetallation of $ICH_2Cl$ to form the anion $LiCH_2Cl$ (i.e. Compound IX) according to Barluenga.

Reaction Scheme 3

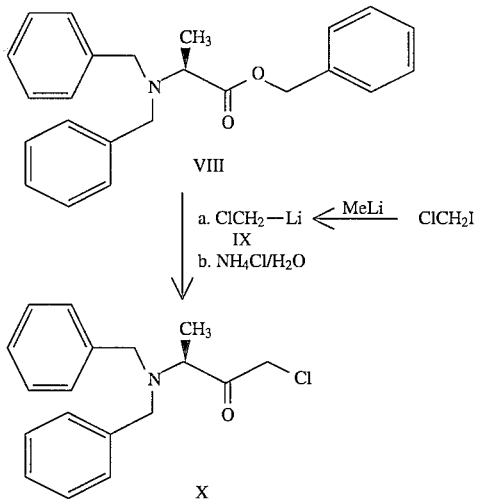

SUMMARY OF THE INVENTION

The present invention relates to a process for preparing an aminoepoxide compound of formula (XV):

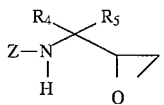
(XV)

wherein $R_4$ and $R_5$ are independently selected from hydrogen, lower alkyl, aryl, aralkyl, substituted lower alkyl, or $R_4$ and $R_5$ are taken together with the carbon atom to which they are bonded to form a substituted or unsubstituted carbocyclo group, which comprises:

(a) reacting a compound of formula (XI)

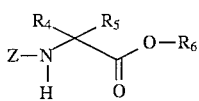
(XI)

wherein Z is a carbamate group having the formula $R_7O_2C—$, wherein $R_7$ is selected from lower alkyl or arylalkyl, and wherein $R_6$ is selected from lower alkyl or benzyl, with at least 2 molar equivalents of a compound of formula (XII):

Li—CHX₁X₂ (XII)

wherein $X_1$ and $X_2$ are independently selected from chloro, bromo, iodo or fluoro, provided at least one of $X_1$ or $X_2$ is bromo or iodo, to form a compound of formula (XIII):

(XIII)

wherein X is selected from $X_1$ or $X_2$; and (b) converting the compound XIII to the aminoepoxide.

A preferred embodiment includes (c) reducing the compound of formula XIII, with or without isolation from the reaction mixture of step (b), to form a halohydrin compound of formula (XIV):

(XIV)

and (d) reacting the halohydrin compound with an alkali metal or amine base to form the aminoepoxide compound of formula (XV).

The halohydrins XIV can form a mixture of diastereoisomers and this application claims the preparation, purification and separation of the mixture and individual isomers.

XIVA

XIVB

Another preferred embodiment is the process wherein 2–5 molar equivalents of the compound of formula XII are used.

Another preferred embodiment is the process wherein step (a) is conducted in the presence of tetrahydrofuran.

Another preferred embodiment is the process wherein $X_1$ is chloro and $X_2$ is iodo.

Another preferred embodiment is the process wherein step (a) is conducted at a temperature in the range of $-30°$ C. to $-100°$ C.

Another preferred embodiment is the process wherein Z is selected from carbobenzyloxy or tertiarybutoxy carbonyl.

Another preferred embodiment is the process wherein the step (c) reduction comprises treating the compound of formula XIII with a hydride reducing agent or a silane reducing agent in the presence of a Lewis Acid.

Another preferred embodiment is the process wherein said hydride reducing agent is sodium borohydride.

Another preferred embodiment is the process wherein the silane reducing agent is $(C_2H_5)_3SiH$ and the Lewis Acid is $BF_3O(C_2H_5)_2$.

Another preferred embodiment is the separation of XIVA and XIVB via crystallization of the mixture from solvents like methanol, ethanol, isopropanol, ethyl acetate, toluene, acetone, water, acetonitrile and mixtures thereof.

Another preferred embodiment is the process wherein $R_6$ is selected from methyl, ethyl or benzyl.

DETAILED DESCRIPTION OF THE INVENTION

In accordance with the present invention, a process is provided in which a compound XI (either available commercially or prepared from I by methods known in the art) of Reaction Scheme 4, where $R_6$ is a lower alkyl group or arylalkyl group, preferably methyl and ethyl, is directly reacted with excess ($\geq 2$ equivalents) of reagent XII, derived from a dihalomethane, preferably chloroiodomethane, and a dialkylamide base, preferably lithium diisopropylamide, to give, after hydrolysis, an N-protected amino acid α-halomethylketone XIII, where Z is a carbamate group, preferably carbobenzyloxy (Cbz) or tertiarybutoxy carbonyl (Boc), and $R_4$ and $R_5$ are independently hydrogen, lower alkyl, aryl, substituted lower alkyl including arylalkyl; $R_4$ and $R_5$ may also be joined together with the carbon atom to which they are bonded to form a carbocyclo group. Intermediate XIII is converted to epoxide XV by reduction with a hydride reducing agent such as sodium borohydride and treatment of the halohydrin intermediate XIV with potassium hydroxide.

Alternatively, the α-halomethylketone XIII produced is reduced 'in situ' (i.e. without isolation) with a hydride reducing agent such as $NaBH_4$ to the halohydrin derivative XIV. This approach has the advantage that it does not require the isolation and purification of the haloketone XIII and avoids the exposure to humans of the toxic products/by-products such as di-halomethanes, trihalomethanes (by-product) and the haloketone.

Alternatively, the halomethylketone XIII produced is stereoselectively reduced with a silane reducing agent, such as $(C_2H_5)_3$ SiH, in the presence of a Lewis Acid such as $BF_3O(C_2H_5)_2$, to the halohydrin derivative XIV. This approach has the advantage that the diastereoisomer XIVA is formed in larger proportion with respect to the diastereoisomer XIVB compared to other reduction conditions such as reduction with sodium borohydride.

As described in Reaction Scheme 4,

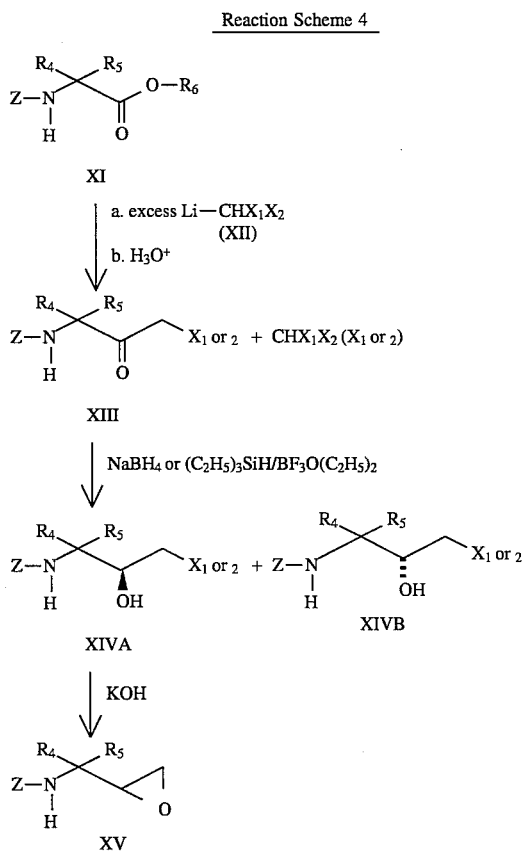

Reaction Scheme 4 a mixture of an N-protected amino ester XI, and from 2 to 5 molar equivalents with respect to XI, preferably 4 equivalents, of a dihalomethane, such as chloroiodomethane, bromoiodomethane, dibromomethane, or diiodomethane, preferably chloroiodomethane, dissolved in an organic solvent such as THF, dioxane, or diethyl ether, preferably, THF, at a temperature within the range of from about −30° to −100° C., preferably −70° to −80° C., under an inert atmosphere such as argon or nitrogen, preferably argon, is treated with 3–6 molar equivalents with respect to XI, preferably 5 equivalents, of a lithium dialkylamide base such as lithium diisopropyl amide, lithium tetramethylpiperidide, or the like, preferably lithium diisopropyl amide, in an organic solvent such as THF, dioxane, or diethyl ether, preferably THF.

Without purification, the isolated α-haloketone XIII is dissolved in an organic solvent such as toluene, THF, isopropanol, ethanol or methanol, or a mixture of these solvents, preferably a mixture which contains toluene:THF:ethanol in ratios from 1:2:1 to 1:1:1, preferably 1:1:1, and is treated with a hydride reducing agent such as sodium borohydride, lithium borohydride, potassium borohydride, diisobutyl aluminum hydride, or the like, preferably sodium borohydride, to give the halohydrin XIV.

Alternatively, the reducing agent is a silane reducing agent in the presence of a Lewis Acid. The silane reducing agent has the formula $(W)_n$ Si $(H)_m$, wherein W is aryl or lower alkyl, n and m are integers from 1 to 3, provided the sum of n and m is 4, —such as $(CH_3)_3$ SiH $(C_2H_5)_3$ SiH or $(Ph)_2SiH2$. The Lewis Acid is well known in the literature and can be for example $BF_3O(C_2H_5)_2$, $ZnCl_2$, $ZnBr_2$, $CF_3COOH$, $MgBr_2$ and the like.

The halohydrin formed (mixture of XIVA and XIVB or individuals) is then purified and separated by crystallization from suitable solvents such as ethanol, methanol, isopropanol, toluene, acetone, acetonitrile, water and mixtures thereof. The resulting halohydrin is then converted to the epoxide XV by methods known in the art.

At the end of the first step, the α-halomethyl ketone produced is reduced with or without isolation and purification of the α-halomethyl ketone. Thus, following quench of the chloroketone reaction mixture with 10 equivalents of acetic acid, adding toluene and warming to −15° C., the mixture is washed sequentially with 1% HCl and 0.5M $NaHCO_3$. The solution is diluted with ethanol, cooled to 0° C. to −78° C. and treated with 4 equivalents of a metal hydride in ethanol as described in the above section.

Preferred N-protected amino ester starting materials XI are those where Z is a substituent which forms a carbamate group, $R_7O_2C$—, where $R_7$ is lower alkyl or arylalkyl, most preferably tertiary butyl and benzyl, such as t-butoxycarbonyl (i.e. Boc) having the formula

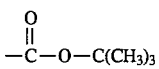

or carbobenzyloxy (i.e. Cbz) having the formula

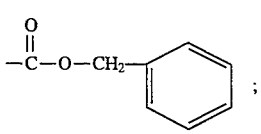

$R_6$ is lower alkyl, or arylalkyl, most preferably methyl, ethyl, and benzyl; and $R_4$ and $R_5$ are independently, hydrogen, lower alkyl, aryl, substituted lower alkyl including arylalkyl; $R_4$ and $R_5$ may also be joined together with the carbon atom to which they are bonded to form a carbocyclo group.

Definitions of terminology used throughout the disclosure herein are provided as follows:

The term "lower alkyl" refers to straight or branched chain hydrocarbon groups having 1 to 6 carbon atoms. Exemplary lower alkyl groups include methyl, ethyl, n-propyl, iso-propyl, n-butyl, iso-butyl, sec-butyl, tert-butyl, n-pentyl, 1-methylbutyl, 2,2-dimethylbutyl, n-hexyl and the like.

The term "substituted lower alkyl" refers to lower alkyl groups, defined above, substituted with 1, 2, or 3 of the following groups:

(1) Hydroxy
(2) Alkoxy
(3) Halo
(4) Aryloxy
(5) —N($R^8$)($R^9$), where ($R^8$) and ($R^9$) are independently hydrogen, alkyl, C(O)$R^7$, C(O)O$R^7$
(6) Aryl
(7) Mercapto
(8) Alkylthio
(9) Arylthio The term "lower alkenyl" refers to straight or branched chain hydrocarbon groups of 2 to 6 carbon atoms having at least one double bond. Exemplary lower alkenyl groups include ethenyl, propenyl, butenyl, pentenyl, hexenyl, and the like.

The term "lower alkynyl" refers to straight or branched chain hydrocarbon groups of 2 to 6 carbon atoms having at least one triple bond. Exemplary lower alkynyl groups include ethynyl, methylethynyl, and the like.

The term "aryl" refers to homocyclic, optionally substituted aromatic groups, preferably monocyclic or bicyclic groups containing 6 to 12 carbon atoms in the ring portion, such as phenyl, naphthyl, tetrahydronaphthyl, indanyl, biphenyl, and the like. Exemplary substituents include 1, 2, or 3 of the following:

(1) Alkoxy
(2) Halo
(3) Alkyl
(4) Alkylthio
(5) Aryloxy
(6) Arylthio
(7) Alkenyl
(8) Alkynyl
(9) Phenyl
(10) —N($R^8$)($R^9$)

(11) 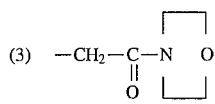

The term "cycloalkyl" refers to a saturated cyclic hydrocarbon group of 3 to 8 carbon atoms such as cyclopropyl, cyclobutyl, cyclopentyl, cyclohexyl, and the like. The term "carbocyclo" refers to a cyclic hydrocarbon group of 3 to 8 carbon atoms, which may be saturated or partially unsaturated, such as cyclopentenyl and the like.

The terms "halogen" or "halo" refer to fluorine, chlorine, bromine and iodine.

The term "alkoxy" denotes an alkyl group bonded through an oxygen bridge (—O—); the term "alkylthio" denotes an alkyl group bonded through a sulfur bridge (—S—); the term "aryloxy" denotes an aryl group bonded through an oxygen bridge (—O—); and the term "arylthio" denotes an aryl group bonded through a sulfur bridge (—S—).

The term "heteroaryl" denotes an aryl group containing 1, 2 or 3 hetero atoms in the ring portion of the group selected from oxygen, sulfur and nitrogen.

The term "substituted carbocyclo" refers to carbocyclo groups defined above, substituted with one of the following groups:

(1) Hydroxy
(2) Benzyloxy (3) 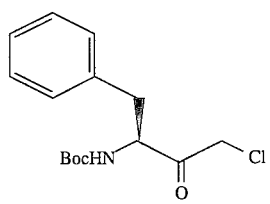

(4) —Si(R)$_3$, where R is lower alkyl

The term "Ph" means phenyl; the term "Bn" means benzyl; the term "Et" means ethyl; the term "Tyr" means tyrosine.

The following examples are offered in order to more fully illustrate the present invention and should not be construed to limit the scope of the invention:

Example 1

(A) Preparation of the chloroketone compound 1 a

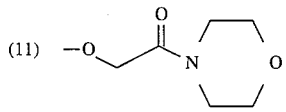

Compound 1a

A solution of lithium diisopropylamide, prepared by adding 2.5M n-butyllithium in hexane (8 mL; 20 mmol) dropwise over 10 minutes to a solution of diisopropylamine (3.1 ml; 20 mmol) in 34 mL of THF at 0° C. and stirring 10 minutes, was added dropwise over 30 minutes through a pressure equalizing addition funnel to a solution of Boc-L-phenylalanine ethyl ester (1.17 g; 4 mmol) and chlor-oiodomethane (1.16 mL; 4 mmol) in 22 mL of THF at −78° C. The internal temperature of the reaction mixture was kept below −70° C. during the addition. After the addition was complete, the reaction mixture was stirred for 10 minutes at −75° C. A solution of acetic acid (6 mL) in 14 mL of THF was then added dropwise over 10 minutes, keeping the internal temperature below −65° C. After stirring an additional 10 minutes at −75° C., the reaction mixture was partitioned between ethyl acetate (150 mL) and brine (150 mL). The organic layer was washed with saturated NaHCO$_3$ solution (2×150 mL), 5% NaHSO$_3$ solution (2×150 mL) and brine (150 mL). Drying over magnesium sulfate and concentration afforded a dark yellow solid, chloroketone 1a.

(B) Preparation of the chlorohydrin compound 1b

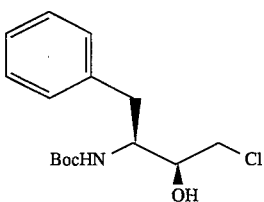

Compound 1b

To the crude 1a prepared as above dissolved in 12 mL of methanol and 12 mL of THF at −15° C. was added portionwise over 30 minutes 212 mg (5.6 mmol) of sodium borohydride. After stirring for 30 min. at −15° C., the reaction was partitioned between 70 mL of saturated KHSO₄ and 200 mL of ethyl acetate and organic layer washed with 150 mL of saturated KHSO₄, saturated NaHCO₃(2×150 mL) and 100 mL brine. Drying over magnesium sulfate and concentration gave a yellow solid which was recrystallized from hot ethyl acetate to afford 612 mg (51%) of a white solid chlorohydrin 1b.

Example 2

(A) Preparation of the chloroketone compound 2a

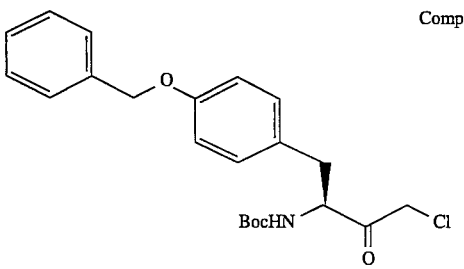

Compound 2a

A solution of lithium diisopropylamide, prepared by adding 2.5M n-butyllithium in hexane (8 mL; 20 mmol) dropwise over 10 minutes to a solution of diisopropylamine (3.1 ml; 20 mmol) in 34 mL of THF at 0° C. and stirring 10 minutes, was added dropwise over 30 minutes through a pressure equalizing addition funnel to a solution of Boc-L-O-benzyltyrosine ethyl ester (1.60 g; 4 mmol) and chloroiodomethane (1.16 mL; 4 mmol) in 22 mL of THF at −78° C. The internal temperature of the reaction mixture was kept below −70° C. during the addition. After the addition was complete, the reaction mixture was stirred for 10 minutes at −75° C. A solution of acetic acid (6 mL) in 14 mL of THF was then added dropwise over 10 minutes, keeping the internal temperature below −65° C. After stirring an additional 10 minutes at −75° C., the reaction mixture was partitioned between ethyl acetate (250 mL) and brine (150 mL). The organic layer was washed with saturated NaHCO₃ solution (2×150 mL), 5% NaHSO₃ solution (2×150 mL) and brine (150 mL). Drying over magnesium sulfate and concentration afforded a dark yellow solid, chloroketone 2a.

(B) Preparation of the chlorohydrin compound 2b

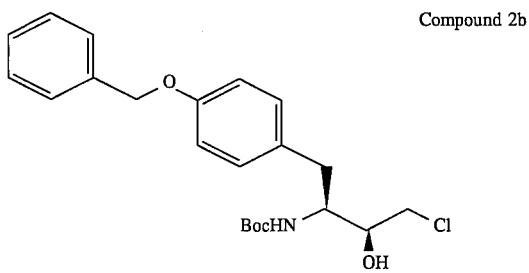

Compound 2b

To the crude 2a prepared as above dissolved in 12 mL of methanol and 12 mL of THF at −15° C. was added portionwise over 30 minutes 228 mg (6.0 mmol) of sodium borohydride. After stirring for 20 min. at −15° C., an additional 85 mg of sodium borohydride was added. After stirring for 25 min. at −15° C., an additional 50 mg of sodium borohydride was added. After 10 minutes, the reaction was partitioned between 70 mL of saturated KHSO₄ and 70 mL of ethyl acetate and the organic layer washed with 70 mL saturated NaHCO₃ and 70 mL brine. Drying over magnesium sulfate and concentration gave a yellow solid which was recrystallized from 3:2 ethyl acetate:hexane to afford 1.03 g (64%) of a white solid chlorohydrin 2b.

Example 3

Preparation of the chlorohydrin (tyrosine series) 2b using the "in-situ" approach

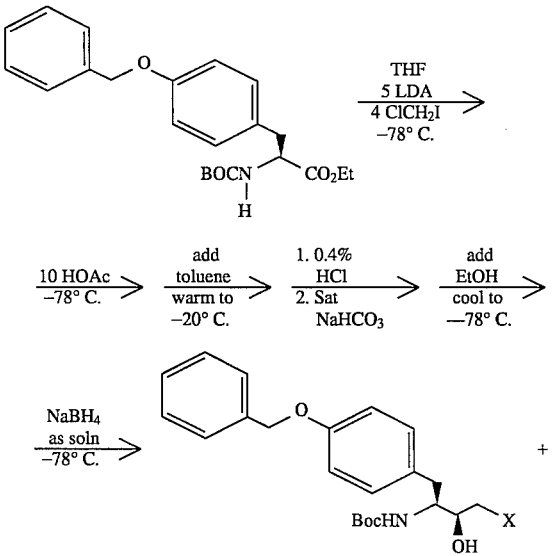

Compound 2b

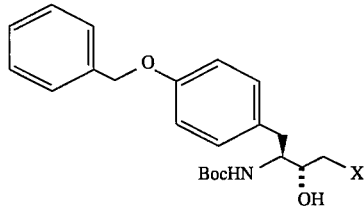

Compound 2c

A 12 L three necked flask was equipped with an overhead mechanical banana type stirring paddle, shaft, and motor. The flask was sealed with septa, a digital thermometer probe was inserted through one of the septa, and the flask was heated to 80° C. (internal air temperature) and purged with nitrogen for 15 min. The flask was charged with N-BOC-L-O-Bn-tyrosine ethyl ester (185.5 g, 0.4643 mol). A 500 mL addition funnel (Ace, needle valve stopcock) was attached to one neck of the flask (Note 1). Tetrahydrofuran (2.53 L, Aldrich, anhydrous, sure-seal) was added to the reaction vessel by direct pouring. The iodochloromethane (328 g, 4 equiv.) was added at once (note 2). The flask was immersed in a dry ice-acetone bath (note 3). The internal temperature was −77° C. The addition funnel was then charged with LDA solution (1.11 L, 2.10M, 5 equiv., Note 4). The LDA solution was then added slowly with stirring (note 5) at a rate which maintained the internal reaction temperature no higher than −75° C. The addition required 2.5 hrs (note 6). During the addition the color of the solution went from clear to yellow to deep burgundy. Upon completion of the addition, the solution was stirred at −77° C. for an additional 2 hrs. Acetic acid solution (325 mL of THF and 325 mL of glacial HOAc) was added dropwise at a rate sufficient to keep the internal temperature of the reaction vessel below −72° C. The addition required 1 hr. Upon completion of the addition, the mixture was stirred an additional 15 min. in the dry ice-acetone bath. At this point toluene (2.0 L, Mallinkrodt Analytical Reagent grade) was added in 25 min. (internal T<−71° C.).

When the internal temperature reached −35° C. (note 7), ice-cold 0.4% aqueous HCl/NaCl(2.5 L, Note 8) was added, and the mixture stirred vigorously to dissolve all salts. This required 10–15 min.

During this time, a dry 2 L Erlenmeyer flask was charged with anhydrous ethanol (1.26L). Solid NaBH$_4$ (49 g, Aldrich) was added, and the mixture was stirred 30 min. at RT. It was cooled to 0° C. under nitrogen before use. When all the salts adhering to the side wall of the 12 L reaction vessel had dissolved, stirring was stopped and the layers allowed to separate. After 10 min., the lower aqueous layer was removed by vacuum suction (note 9). The washing with HCl/NaCl(2.0L) was repeated one more time at RT. Then, sat. NaHCO$_3$(2.0 L) was added, and the mixture stirred vigorously for 10 min. The layers were allowed to settle. The lower aqueous layer was separated as above. The wash with sat NaHCO$_3$(2.0 L) was repeated one more time. Anhydrous ethanol (1.26 L, note 10) was added, stirring initiated, and the flask was immersed in a dry ice-acetone cooling bath. When the temperature reached −75° C., the previously prepared ethanolic NaBH$_4$ solution was cannulated into the reaction mixture under a positive pressure of nitrogen. The internal temperature of the reaction vessel did not get higher than −68° C. The addition required 1 hr. The reaction vessel was stirred at −78° C. for 13 hrs (note 11 ), warmed to 0° C. and stirred for 2 hrs (note 12). The color of the solution lightened upon warming. After 2 hrs at 0° C., the reaction was quenched by addition of a solution of 0.7 L saturated KHSO$_4$. The mixture was stirred at 0° C. for 30 min, then poured into a 20 L single necked flask, diluted with 0.7 L water and concentrated in vacuo to ~half its volume. More water (0.7 L) was added to dissolve KHSO$_4$ precipitates and concentration was continued for 3 hrs (bath T<30° C.) to ~2 L volume. The resultant mixture was stirred by means of an overhead mechanical stirrer for 30 min. The solid was collected by pouring onto a glass frit with suction filtration. The solid was quantitatively transferred and rinsed with the aid of an additional 300 mL×3 of water. The yellow solid was then rinsed with 300 mL×3 of hexane (note 13), and dried overnight by suction filtration. This process afforded a yellow solid, 205 g, with diastereomeric ratio of 3.5:1 (note 14).

The solid was taken up in hot 95% EtOH (3.0 L, 74° C.), cooled briefly, charcoal (10 g, Norit, Fisher, neutral) added, the mixture heated for 5 min with swirling, and finally filtered through celite. The flask was washed with additional hot EtOH (4×125 mL), which was then used to rinse the celite pad. The flask was heated to dissolve all solid in a water bath at 74° C. The bath was allowed to slowly cool to room temperature overnight. The flask was placed in the cold room (~5° C.). After 20 hrs, water (0.4 L) was added and the mixture was stirred for 3 hrs at RT. It was then filtered and washed with 100 ml×3 hexanes. The material was collected as a fine yellowish solid: 95 g, 50%. HPLC analysis indicated a diastereomeric ratio of 96.8:3.2(2b:2c).

Notes:

1. The addition funnel should be positioned to deliver the LDA solution as close as possible to the center of the reaction vessel. This tends to minimize splashing onto the walls of the reaction vessel. The needle valve on the addition funnel provides optimum control over the addition rate of the LDA solution.

2. ClCH$_2$I comes in a sealed bottle, 25 g each. A total of 13.5 bottles were used.

3. During the addition of LDA to the −78° C. solution of BOC-OBnTyr-OEt and ClCH$_2$I, lithiochloromethide anion was generated. It is very unstable and must be kept as cold as possible. If the solution splashes onto the walls of the flask two things happen: (a) a solid deposits itself on the walls of the flask, and (b) the lithiochloromethide warms up. Empirically, both phenomena appear to be detrimental to yield and product purity. The reaction flask should be immersed in the cooling bath as much as possible to keep the splashing cold.

4. LDA lot #3033 was obtained from FMC Lithium Division and was titrated using diphenylacetone fosylhydrazone according to Lipton, M. F. et al *J. Organomet. Chem.*, 1980, 186, 155.

5. It might take a long time to finish the addition of LDA while keeping the internal temperature below −75° C., if the stirring is too slow.

6. After addition of the first 500 ml of LDA, the addition funnel was recharged with more LDA and the addition continued until all LDA was added.

7. To speed up the warming process, the acetone-dry ice bath was replaced with an acetone-water bath.

8. The solution was prepared by dissolving 1 mL of concentrated HCl in 50 mL of water and 50 mL of brine.

9. It was not easy to see the separation of the phases in the round bottom flask when there was not much aqueous solution remaining. It is recommended to collect 750 ml of solution into a separatory funnel when the organic layer reaches the bottom. New phase separation would form in the separatory funnel and the top organic layer could be put back to the reaction flask. It is important to wash away all of the HOAc, Li salt and diisopropylamine as their presence decrease the selectivity of reduction. If necessary, the wash should be conducted in a phase splitter and not in the reaction flask.

10. To save time, the ethanol was precooled to −78° C. under nitrogen.

11. The reductions were also carried out on smaller scales (1–10 g) without overnight stirring and similar results were obtained. I this case it was more convenient to let the reduction go overnight at −78° C.

12. This is to destroy iodine related impurities (if any) and to ensure complete reduction.

13. The solid thus obtained is not very soluble in hexanes. There was not much weight loss after wash with hexanes.

14. There could be two reasons for the low ratio: (a) the aqueous wash in the reaction flask was not very effective. (b) substantial amount of the correct iodohydrin was formed which behaves similarly to the minor isomer of chlorohydrin, in which case, the iodohydrin could be converted to the desired epoxide.

Example 4

Preparation of the chlorohydrin (phenylalanine series) 1b using the "in-situ" approach

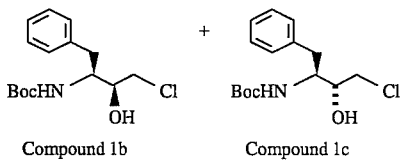

Compound 1b    Compound 1c

Iodochloromethane (180 mL, 4 equiv.) was added to a solution of N-BOC-L-phenylalanine ethyl ester (175.8 g, 0.6 mol) in anhydrous tetrahydrofuran (1500 mL). The flask was cooled to −78° C. and LDA solution (1333 mL, 5 equiv., 2.25M) was then added slowly with very gentle stirring. Upon completion of the addition, the solution was stirred at −78° C. for an additional 15 min.

Acetic acid solution (330 mL of THF and 330 mL of glacial HOAc) was added dropwise at a rate sufficient to keep the internal temperature of the reaction vessel below −68° C. Upon completion of the addition, the mixture was stirred an additional 15 min. in the dry ice-acetone bath. The cooling bath was then removed and the flask slowly allowed to warm. At this point toluene (1500 mL) was added.

When the internal temperature reached −20° C., the mixture was washed sequentially with ice-cold 1% aqueous HCl (1500 mL) and ice cold 0.5M NaHCO$_3$ (1500 mL). Anhydrous ethanol (1500 mL) was added, stirring initiated, and the flask cooled to −74° C., a solution of NaBH$_4$ (60g) in anhydrous ethanol (2000 mL) was added.

The reaction vessel was stirred at −78° C. for 12 h, warmed to 0° C. and stirred for 2 h. After 2 h at 0° C., the reaction was quenched by addition of a solution of [750 mL saturated KHSO$_4$+750 mL of water]. The mixture was stirred at 0° C. for 30 min, and evaporated in vacuo. Water (3000 mL) was added to the solid yellow residue, and the resultant mixture stirred 30 min. The solid was collected and rinsed an additional 1000 mL of water. The yellow solid was then rinsed three times with hexane (400 mL, then 600 mL, then 400 mL), and dried overnight by suction filtration. This process afforded a yellow solid, 136.1 g (76%), which analyzed by HPLC as a 9:1 mixture of (1b:1c) diastereomers.

The solid was taken up in hot ethyl acetate (2700 mL), cooled briefly, charcoal (8.1 g, Norit, Fisher, neutral) added, the mixture heated for 5 min with swirling, and finally filtered through celite. The flask was washed with additional hot ethyl acetate (200 mL, then 50 mL), which was then used to rinse the celite pad. The ethyl acetate filtrate was then concentrated to 1700 mL in vacuo, the mixture heated briefly to redissolve the chlorohydrins, and the flask sealed and placed in a preheated water bath at 40° C. The bath was maintained at 40° C. for 2 h, then allowed to slowly cool to room temperature and then at −5° C. The material was collected as brown mossy crystals: 81.7 g, 45.5%. HPLC analysis indicated a diastereomeric ratio of chlorohydrin compound 1b:95.6: incorrect chlorohydrin 1c:2.0: correct iodohydrin 1.0.

Example 5

Preparation of the epoxide (phenylalanine series)

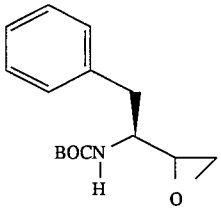

A solution of potassium hydroxide in ethanol (328 mL, 1M) was added to a solution of N-BOC-L-phenylalanine chlorohydrin 1b (81.7 g, 0.27 mol) in anhydrous ethanol (2800 mL). The suspension was stirred at ambient temperature for 2 h. A solution of NaH$_2$PO$_4$.H$_2$O(18.8 g) in water (320 mL) was added and the mixture placed on a rotary evaporator. When the majority of the ethanol was removed, the slurry was partitioned between ethyl acetate (1500 mL) and water (500 mL). The aqueous layer was extracted with ethyl acetate (500 mL). The combined ethyl acetate extracts were dried (MgSO$_4$), filtered and concentrated. The brown solid was dissolved in hot hexane (5.4 L), and filtered through a plug of glass wool. The filtrate was reheated to redissolve the epoxide. The solution was allowed to stand at room temperature and then placed in a cold room and finally in a freezer at −5° C. The epoxide was collected as needles, 62.1 g, 85%.

Example 6

Preparation of the epoxide (tyrosine series)

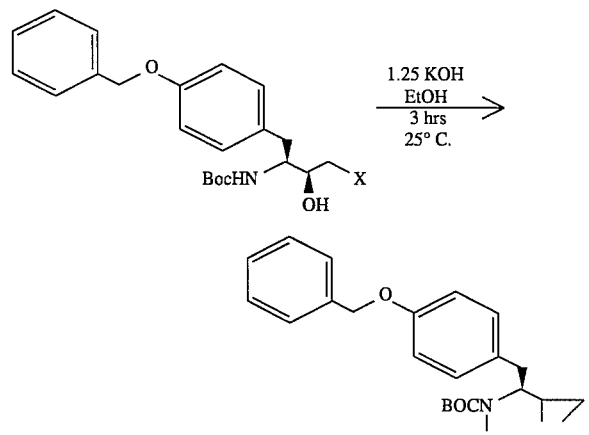

Anhydrous ethanol was obtained from Quantum Chemical Company. Potassium hydroxide (pellets, 87.8%) was obtained from Mallinckrodt and used without further purification.

A dry 4 L Erlenmeyer flask was charged with N-BOC-L-O-benzyl-tyrosine chlorohydrin 2b (82 g, 202 mmol, note 1). Anhydrous ethanol (1.6 L) was added. With stirring and under nitrogen, a solution of potassium hydroxide in ethanol (31.1 mg/1 ml, 520 ml, 1.25 equiv.) was added to the resulting suspension in 10 minutes. The suspension was stirred at ambient temperature for 3 hrs. When the reaction was complete (note 2), the excess KOH was neutralized with addition of aqueous KH$_2$PO$_4$(10.5 mg/1 ml, 130 ml, 0.5 equiv., note 3). The mixture was transferred to a 2 L round bottom flask and concentrated to 1 L in volume (note 4). The ethanolic solution was diluted with brine. (1 L). Precipitation occurred immediately. The resulting mixture was stirred at RT for 30 min. and then filtered. The solid cake was washed with water (500 ml×3). Precipitation also occurred when the washings were combined with the original filtrate. The resulting solid was collected as second crop, washed with water (100 ml×3) and combined with the first crop. The combined solid was washed with hexanes (300 ml×3) and dried overnight (13 hrs)by suction filtration to give 77 g yellow solid (note 5).

Optional Crystallization Purification is as follows:

The solid was combined with another batch (note 6) to give a total of 112 g. The combined material was dissolve in toluene (1 L) at RT (note 7), charcoal (15 g) was added and the mixture was stirred for 30 min, then filtered through a pad of celite. The flask was washed with additional hot toluene (50° C., 100 ml×2), which was then used to rinse the celite pad. With stirring, heptane (2.5 L) was added to the toluene solution. The resulting clear solution was seeded and set aside at RT overnight (13 hrs). The crystals were stirred in the solvents for 3 hrs and heptane (0.5 L) was added in the mean time. The mixture was then filtered and washed with hexanes (150 ml×2) to give 79 g of an off-white solid (little yellow), with an overall yield of 71% (note 8).

Notes:

1. The chlorohydrin had a diastereomeric ratio of 96.8:3.2(2b:2c).

2. The reaction should be monitored by HPLC. S. M. and product retention times differ by 1 min. If the reaction is not complete in 3 hrs, addition of more EtOH and/or KOH solution (0.1–0.5 equiv.) will accelerate the reaction to completion.

3. The excess KOH (or KOEt) will generate impurities by opening the epoxide during the course of concentration.

4. The bath temperature was kept at 30°–35° C. In the end, some solid had precipitated out.

5. The yield is quantitative. The diastereomeric ratio was 96.5:3.5.

6. This batch with a diastereomeric ratio (97:3) was obtained from 41 g of chlorohydrin (95.4:4.6), which in turn was obtained by recrystallization of second crop of the combined mother liquor of 3 batches of chlorohydrin.

7. There is some residual oily material not completely dissolved in toluene. It was removed by filtration after the charcoal treatment. This was not observed when the recrystallization was conducted in EtOAc and hexanes.

8. The HPLC diastereomeric ratio of the final product is 98.5:1.5. To increase yield, the volume of toluene may be reduced, in which case, heating the solution to higher temperature may be needed to dissolve all material.

Example 7

(A) Preparation of the chloroketone compound 1a

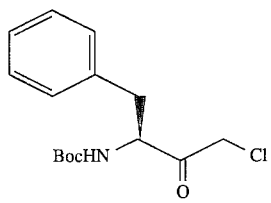

Compound 1a

A solution of LDA in THF (100 mL, 2.04M, 5 equiv.) was added dropwise to a −78° C. solution of N-BOC-Phe-OEt (11.72 g, 40 mmol) and ClCH$_2$I (12 mL, 4 equiv.) in tetrahydrofuran (625 mL). After the addition was complete, the mixture was stirred for 20 min. and quenched by dropwise addition of HOAc (25 mL) in THF (50 mL). After 10 min, the mixture was slowly allowed to warm to RT and water (400 mL) was added. The organics were removed in vacuo, and the residue partitioned between itself and 80:20 ethyl acetate:hexane. The organic layer was washed sequentially with 5% NaHCO$_3$ (300 mL) and 5% NaHSO$_3$ (200 mL), dried (MgSO$_4$), filtered, and concentrated. The residue was triturated with diethyl ether (250 mL), and the ether refluxed gently for 5 min. in the presence of 2.4 g of charcoal, filtered through 0.75" by 2.5" of celite, and concentrated to afford a yellow solid.

Recrystallization from hot ethyl acetate (16 mL) and hexane (200 mL) by cooling to RT and then 5° C. afforded the chloroketone 1a as light yellow mossy needles: 6.82 g, 57.4%.

(B) Preparation of the chlorohydrin compound 1b

General metal hydride reduction procedure:

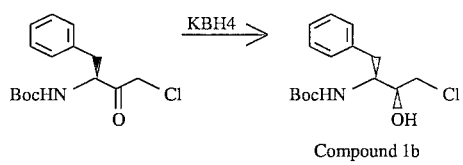

Compound 1b

Solid KBH$_4$ (59.7 mg) was added at −20° C. to a solution of the chloroketone (297 mg, 1 mmol) in methanol (2 mL) and THF (2 mL). After 5 min, THF (1 mL) was added and the suspension warmed to 0° C. After 1 h, a saturated solution of KHSO$_4$ (11.75 mL) was added followed by ethyl acetate (15 mL). The mixture was transferred to a separatory funnel with the use of water (5 mL) and ethyl acetate (10 mL), the phases shaken and separated. The organic layer was washed with 5% NaHCO$_3$ and 5% NaHSO$_3$, dried (MgSO$_4$), filtered and concentrated to afford 284.3 mg (95%) of an off white solid. The solid was recrystallized from 12 mL of hot 50:50 ethyl acetate:hexane to afford the chlorohydrin 1b as needles:159.2 mg (53%). Similar results were obtained with sodium borohydride.

Example 8

Preparation of BOCN(H)-O-Bn-Tyr-Chloroketone, Compound 2a

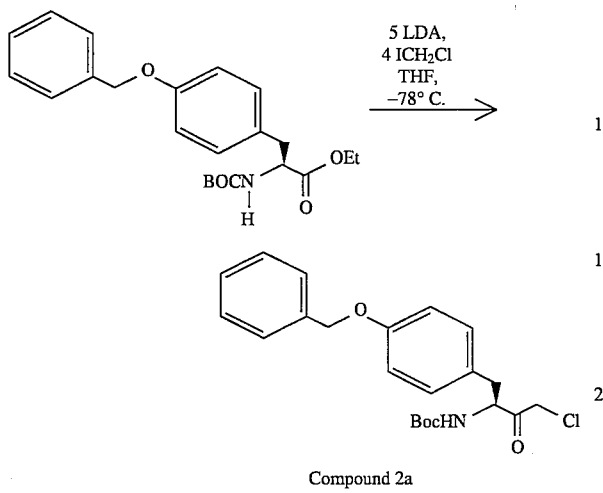

Compound 2a

A 1 L three neck oven dried, argon purged flask was charged with N-BOC-L-O-Bn-tyrosine ethyl ester (10.0 g, 25.03 mmol). The flask was equipped with an overhead mechanical stirrer. A 100 mL addition funnel was attached to one neck of the flask. The flask was sealed with septa, a digital thermometer probe was inserted through one of the septa. Anhydrous tetrahydrofuran (375 ml, freshly distilled) was added to the reaction vessel via a syringe. The iodochloromethane (17.66 g, 4 equiv.) was added at once under argon. The flask was immersed in a dry ice-acetone bath. The internal temperature was −77° C. The addition funnel was then charged with LDA solution (62.5 mL, 2.0M, 5 equiv., titrated prior to use). The LDA solution was then added slowly with stirring at a rate which maintained the internal reaction temperature no warmer than −73° C. The addition required 1 hr. During the addition the color of the solution went from clear to yellow to deep burgundy. Upon completion of the addition, the solution was stirred at −77° C. for an additional 0.5 hrs.

Acetic acid solution (89 mL of THF and 19 mL of glacial HOAc) was added dropwise at a rate sufficient to keep the internal temperature of the reaction vessel below −71° C. The addition required 0.5 hrs. Upon completion of the addition, the mixture was stirred an additional 15 min. in the dry ice-acetone bath. It was transferred to a 2 L round bottom flask. Water (400 ml) was added. The mixture was evaporated to a clear two layer system. It was diluted with EtOAc (500 ml), transferred back to a 2 L separatory funnel and washed with brine (400 ml×2).

The organic layer was concentrated to a dark colored solid, which was then dissolved in acetonitrile (100 ml) and washed with hexanes (100 ml×3). The acetonitrile layer was diluted with toluene (400 ml), washed Na$_2$SO$_3$ (5% in brine, 400 ml×2). The aqueous layer was extracted with toluene (200 ml). The combined organic layers were washed with brine (400 ml×2), dried over MgSO$_4$ and concentrated to a dark colored solid (13.5 g), which was dissolved in toluene (40 ml). Hexanes (70 ml) was added with heating. The resulting clear solution was seeded and put aside at room temperature overnight. Crystallization occurred and the resulting solid was collected by filtration and washed with hexanes (8ml×2) affording a yellow powder (6.5 g, 65% yield).

Example 9

Preparation of BOCN(H)-O-Bn-Tyr, Chlorohydrin,. Compound 2b

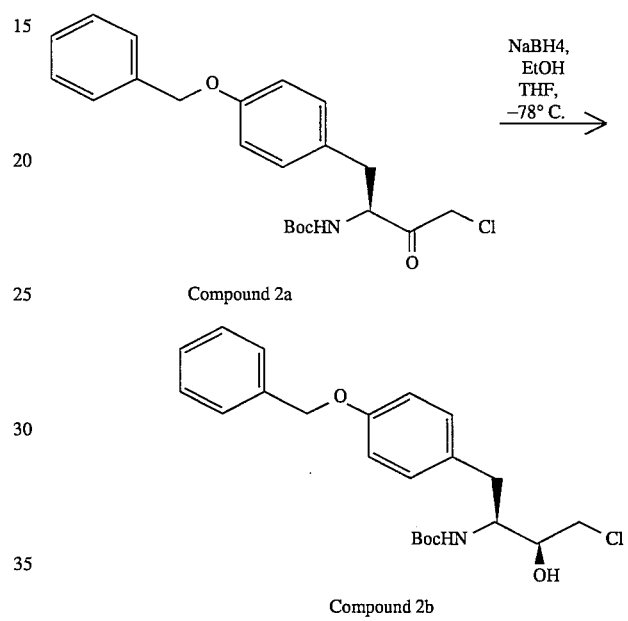

A 50 ml round bottom flask was charged with sodium borohydride (235 mg, 6.31 mmol). Anhydrous ethanol was added under argon. The resulting suspension was stirred at room temperature for 15 min. then cooled to −78° C. A solution of N-BOC-L-O-Bn-tyrosine chloroketone in THF (5 ml) and EtOH (5 ml) was added dropwise through a syringe in 30 min. The internal temperature did not rise above −70° C. during the course of the addition. The reaction mixture was stirred at −78° C. for 2 hrs. It was diluted with dropwise addition of EtOAc (200 ml). The mixture was allowed to warm up to 0° C. and and KHSO$_4$ (half saturated, 100 ml) was added. After stirring at 0° C. for 15 min, the mixture was transferred to a 500 mL separatory funnel and washed with KHSO$_4$ (half saturated, 100 ml×2) and brine (100 ml×2). The organic layer was dried over MgSO$_4$ (10 g). It was filtered and concentrated to a white solid (1.2 g, diastereomeric ratio 5:1), which was dissolved in hot EtOAc (16 ml). The resulting clear solution was put aside at room temperature for 16 hrs then at 0° C. for 16 hrs.

Crystallization occurred. The desired product was collected by filtration as white solid (0.65 g, diastereomeric ratio 95:5).

Example 10

Preparation of BOCN(H)-O-Bn-Tyr-Chlorohydrin, Compound 2b

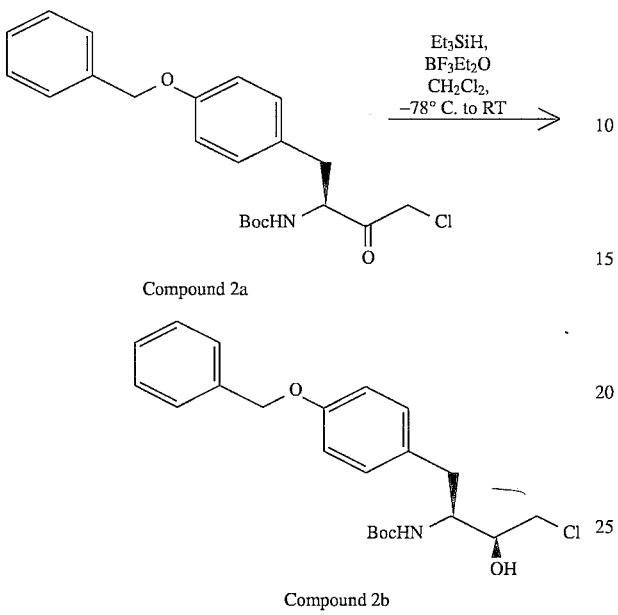

Compound 2a

Compound 2b

A 50 ml oven dried, argon purged round bottom flask was charged with N-BOC-L-O-Bn-tyrosine chloroketone (1.0 g, 2.48 mmol). $CH_2Cl_2$ (15 ml) was added. The resulting solution was cooled to −78° C. under argon. $Et_3SiH$ was added followed by dropwise addition of $BF_3$ etherate at −78° C. in 5 min. The reaction mixture was stirred at −78° C. for 2 hrs and slowly warmed to room temperature and stirred at room temperature for another 2 hrs. It was recooled to −78° C. A solution of NaOAc (5 g) in MeOH (10 ml) was added dropwise through a syringe in 15 min. (T<−60° C.). The reaction mixture was then stirred at 0° C. for 1 hr and was transferred to a 250 ml round bottom flask. $NaHCO_3$ (sat., 50 ml) followed by $(BOC)_2O$ (0.54 g, 1 equiv.) was added. The mixture was stirred at room temperature for 2 hrs. It was diluted with EtOAc (80 ml), transferred to a 250 ml separatory funnel and washed with $KHSO_4$ (half sat., 30 ml×2), $NaHCO_3$ (sat., 30 ml×2) and brine (30 ml×2). The organic layer was dried over $MgSO_4$ (5 g), filtered and concentrated to give 1.5 g of wet solid, which was dissolved in hot EtOAc (15 ml) and put aside at room temperature for 10 hrs then at 4° C. for 3 days. Crystallization occurred. The solid was collected by filtration and washed with hexanes. The desired product was obtained in 60% yield as the first crop (HPLC showed de of 99+%).

The mother liquor was concentrated. The residue was dissolved in hot EtOAc (2 ml). The resulting clear solution was seeded and put aside at room temperature for 16 hrs and at 4° C. for 2 days. The desired product was obtained as second crop in 20% yield (HI: 95%, de: 99+%).

What is claimed is:

1. A process for preparing an aminoepoxide compound of formula (XV)

wherein $R_4$ and $R_5$ are independently selected from hydrogen, lower alkyl, aryl, aralkyl substituted lower alkyl, or $R_4$ and $R_5$ are taken together with the carbon atom to which they are bonded to form a substituted or unsubstituted carbocyclo group, which comprises:

(a) reacting a compound of formula (XI)

wherein Z is a carbamate group having the formula $R_7O_2C-$, wherein $R_7$ is selected from lower alkyl or arylalkyl, and wherein $R_6$ is selected from lower alkyl or benzyl, with at least 2 molar equivalents of a compound of formula (XII):

$$Li-CHX_1X_2 \quad (XII)$$

wherein $X_1$ and $X_2$ are independently selected from chloro, bromo, iodo or fluoro, provided at least one of $X_1$ or $X_2$ is bromo or iodo, to form a compound of formula (XIII):

wherein X is selected from $X_1$ or $X_2$; and (b) converting the compound XIII to the aminoepoxide.

2. The process of claim 1 wherein step (a) is carried out in the presence of tetrahydrofuran.

3. The process of claim 2 wherein step (b) comprises:

(c) reducing the compound of formula XIII to form a halohydrin compound of formula (XIV):

and (d) reacting the halohydrin compound with an alkali metal or amine base to form the aminoepoxide compound of formula (XV).

4. The process of claim 3 wherein 2–5 molar equivalents of the compound of formula XII are used.

5. The process of claim 3 wherein $X_1$ is chloro and $X_2$ is iodo.

6. The process of claim 3 wherein step (a) is conducted at a temperature in the range of −30° C. to −100° C.

7. The process of claim 3 wherein Z is selected from carbobenzyloxy or tertiarybutoxy carbonyl.

8. The process of claim 3 wherein the step (c) reduction comprises treating the compound of formula XIII with a hydride reducing agent.

9. The process of claim 8 wherein said hydride reducing agent is sodium borohydride.

10. The process of claim 3 wherein R6 is selected from methyl, ethyl or benzyl.

11. The process of claim 3 wherein step (c) is carried out in situ.

12. The process of claim 3 wherein step (c) further comprises recovering the halohydrin isomer XIVA

and step (d) comprises reacting compound XIVA with an alkali metal base to form the aminoepoxide compound of 13. The process of claim 3 wherein step (c) comprises stereoselectively reducing the compound of formula XIII to form a halohydrin compound of formula XIVA

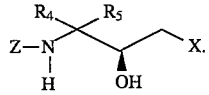

(XIVA)

14. The process of claim 3 wherein the step (c) reduction comprises treating the compound of formula XIII with a silane reducing agent in the presence of a Lewis Acid.

15. The process of claim 14 wherein the silane reducing agent has the formula $(W)_n Si(H)_m$ wherein W is aryl or lower alkyl; and n and m are integers from 1 to 3, provided the sum of n and m is 4.

16. The process of claim 15 wherein the silane reducing agent is $(C_2H_5)_3SiH$ and the Lewis Acid is $BF_3O(C_2H_5)_2$.

* * * * *